United States Patent [19]
Keggenhoff et al.

[11] Patent Number: 4,597,909
[45] Date of Patent: Jul. 1, 1986

[54] PROCESS FOR THE PRODUCTION OF POLYISOCYANATES

[75] Inventors: Berthold Keggenhoff; Enno Mählmann, both of Krefeld; Willi Eifler, Bergisch-Gladbach; Günther Ellendt, Krefeld, all of Fed. Rep. of Germany

[73] Assignee: Bayer Aktiengesellschaft, Leverkusen, Fed. Rep. of Germany

[21] Appl. No.: 703,843

[22] Filed: Feb. 21, 1985

[30] Foreign Application Priority Data

Mar. 1, 1984 [DE] Fed. Rep. of Germany ....... 3407494

[51] Int. Cl.$^4$ .......................................... C07C 118/02
[52] U.S. Cl. ................... 560/347; 560/359; 564/333
[58] Field of Search ................ 564/333; 260/453 PH, 260/453 AM

[56] References Cited

U.S. PATENT DOCUMENTS 3,367,969 2/1968 Perkins .............................. 260/570
4,259,526 3/1981 Dunlap et al. ..................... 564/331

Primary Examiner—Dolph H. Torrence
Attorney, Agent, or Firm—Gene Harsh; Joseph C. Gil

[57] ABSTRACT

The present invention is directed to a process for the production of polyamines of the diphenylmethane series having a high diamine content and a low 2,2'-diaminodiphenylmethane content by condensing aniline with formaldehyde in the presence of hydrochloric acid as catalyst, neutralizing the acid catalyst at the end of the condensation reaction and working up the polyamine mixture thus obtained by distillation, characterized in that (a) in a first reaction stage, from 2.0 to 3.5 moles of aniline are reacted with 1 mole of formaldehyde in the presence of hydrochloric acid or a condensation product produced from 2.0 to 3.5 moles of aniline and 1 mole of formaldehyde in the absence of acid catalyst is reacted in the presence of hydrochloric acid at a degree of protonation maintained at 40 to 60% at temperatures below 50° C., (b) more aniline is then added to the reaction mixture so that the molar ratio of amine nitrogen atoms in the form of free aniline and the reaction products formed in accordance with (a) to formaldehyde chemically bound in the form of methylene bridges in those reaction products rises to more than 10:1 and up to 20:1 with the degree of protonation decreasing correspondingly, (c) the reaction mixture obtained in accordance with (b) is heated to allow the N-substituted intermediate products present to be completely rearranged into polyamines containing unsubstituted primary amino groups, and (d) the reaction mixture obtained in accordance with (c) is worked up by distillation after neutralization of the acid.

The invention is also directed to the use of the polyamines so produced in the manufacture of polyisocyanates.

5 Claims, No Drawings

PROCESS FOR THE PRODUCTION OF POLYISOCYANATES

BACKGROUND OF THE INVENTION

The present invention relates to a new process for the production of polyamines of the diphenylmethane series having a high diamine content and a low 2,2'-diaminodiphenylmethane content by reacting aniline with formaldehyde in two stages in the presence of hydrochloric acid as catalyst.

Polyisocyanate mixtures of the diphenylmethane series having a diisocyanate content of more than 85% have become increasingly interesting from a commercial standpoint for use in making polyurethanes, since they are only just below the high-purity diisocyanates in terms of quality, but can be produced much more economically. As far as their properties are concerned, it has often proved to be favorable for them to have an average 2,4'-diisocyanato-diphenylmethane content of from about 8 to 12% because their tendency towards crystallization is thus suppressed without any significant reduction in their reactivity. The production of the high-diamine polyamines on which these isocyanates are based is known in principle in the art. They are obtained by carrying out the condensation of aniline with formaldehyde, using a high molar ratio of aniline to formaldehyde.

A significant cost factor in the commercial manufacture of these products is the quantity of hydrochloric acid used because, normally, the hydrochloric acid must be removed from the process by the addition of sodium hydroxide.

The degree of protonation is the percentage of the amino groups present in the form of ammonium groups (i.e. amino groups neutralized with hydrochloric acid) based on the total quantity of all the amino groups (i.e. neutralized and non-neutralized amino groups in the reaction mixture). If a low degree of protonation is selected in order to obtain economically favorable consumptions of hydrochloric acid and sodium hydroxide (despite the high excess of aniline required to obtain the high diamine content), not only are increased contents of 2,4'-diamino-diphenylmethane obtained (which may often be desirable) but 2,2'-diamino-diphenylmethane is also formed to a greatly increased extent. This component leads not only to a distinct reduction in the reactivity of the polyisocyanate mixture produced from the polyamines, but it also has an adverse effect upon the properties of the polyurethane plastics produced from those polyisocyanates.

U.S. Pat. No. 3,367,969 describes a process for the production of polyamine mixtures of the diphenylmethane series comprising (i) reacting from 1.5 to 6 moles (and preferably from 2 to 5 moles) of aniline with 1 mole of formaldehyde in the presence of from 0.25 to 1.1 mole (and preferably from 0.95 to 1.05 moles) of hydrochloric acid per mole of aniline at 20° to 50° C.; (ii) subsequently adding at least 0.2 mole of aniline so that, in its final composition, the mixture contains from about 2 to about 10 moles (and preferably from about 2.5 to about 5 moles) of aniline per mole of formaldehyde and from about 0.1 to 0.98 mole (and preferably from 0.75 to 0.95 mole) of hydrochloric acid per mole of aniline; and (iii) heating the mixture to 50°-100° C. until the reaction is complete. After the acidic reaction mixture thus obtained has been neutralized, excess aniline is separated off and the 4,4'-diamino-diphenylmethane is recovered by distillation. This method of producing pure 4,4'-diaminodiphenylmethane is attended by the disadvantage that secondary products, particularly in the form of polyamines of relatively high functionality (distillation residue), accumulate in considerable quantities.

In all but one of the examples of the above-mentioned U.S. Pat., a degree of protonation of 100% (i.e., a slight excess of hydrochloric acid is used) is maintained in the first stage and a degree of protonation of at least 50% is maintained in the second stage of the reaction. Quite apart from the high consumption of hydrochloric acid and the sodium hydroxide required for its neutralization, a procedure such as this leads to a polyamine mixture from which 4,4'-diamino-diphenylmethane can admittedly be isolated in a high yield. If, however, the 4,4'-diamino-diphenylmethane is not isolated, the polyamine mixture is attended by the disadvantage that the corresponding phosgenation product (i.e., the corresponding polyisocyanate mixture) shows a pronounced tendency towards crystallization at room temperature and has a relatively high chlorine content. Finally, the corresponding polyisocyanate mixtures are dark in color.

The object of the present invention is to provide a new process for the production of polyamines of the diphenylmethane series by which it is possible to produce polyamines which contain at least 89% by weight of diamines and from 8 to 12% by weight of 2,4'-diamino-diphenylmethane content. The resultant polyamines may be used for producing the corresponding polyisocyanate mixtures which are distinguished by high reactivity, have a minimal tendency towards crystallization and which are light in color. At the same time, the new process utilizes relatively small quantities of hydrochloric acid catalyst.

DESCRIPTION OF THE INVENTION

The present invention is directed to a process for the production of polyamines of the diphenylmethane series having a high diamine content and a low 2,2'-diaminodiphenylmethane content by condensing aniline with formaldehyde in the presence of hydrochloric acid as catalyst, neutralizing the acid catalyst at the end of the condensation reaction and working up the polyamine mixture thus obtained by distillation, characterized in that (a) in a first reaction stage, from 2.0 to 3.5 moles of aniline are reacted with 1 mole of formaldehyde in the presence of hydrochloric acid or a condensation product produced from 2.0 to 3.5 moles of aniline and 1 mole of formaldehyde in the absence of acid catalyst is reacted in the presence of hydrochloric acid at a degree of protonation of 40 to 60% at a temperature below 50° C., (b) more aniline is subsequently added to the reaction mixture so that the molar ratio of amine nitrogen atoms in the form of free aniline and the reaction products formed in accordance with (a) to formaldehydes chemically bound in the form of methylene bridges in those reaction products increases to more than 10:1 and up to 20:1 with the degree of protonation decreasing accordingly, (c) the reaction mixture obtained in accordance with (b) is heated to allow the N-substituted intermediate products present to be completely rearranged into polyamines containing unsubstituted primary amino groups, and (d) the reaction mixture obtained in accordance with (c) is worked up by distillation after neutralization of the acid.

Starting materials for the process according to the invention are aniline, formaldehyde in the form of aqueous (normally 30 to 50% by weight) solutions and hydrochloric acid, normally in a concentration of from 30 to 37% by weight.

In the first reaction stage, the starting materials are used in quantitative ratios corresponding to a molar ratio of aniline to formaldehyde of from 2:1 to 3.5:1 and preferably from 2.5:1 to 3:1 and to a degree of protonation of from 40 to 60%. The quantity of the aniline added in the second reaction stage is thus gauged in such a way that, in the reaction mixture, the molar ratio of amine nitrogen atoms to formaldehyde (already chemically bound therein in the form of methylene bridges) is greater than 10:1 and up to 20:1 and preferably between 11:1 and 16:1 with the degree of protonation of the further addition of aniline correspondingly reduced.

In the first reaction stage, the reaction temperature is below 50° C., preferably in the range from 30° to 40° C. and, more preferably, in the range from 32° to 38° C. The reaction mixture of the first reaction stage to which more aniline is added is then gradually heated in the second reaction stage to a final temperature of at least 100° C., preferably of at least 130° C. and, more preferably, in the range from 130° to 150° C. under an excess pressure which at least corresponds to the particular vapor pressure of the mixture.

The residence time (or, in the event of continuous working, the average residence time) of the reaction mixture in the first reaction stage should amount to at least 15 minutes and preferably to between 30 and 90 minutes. The (average) residence time of the reaction mixture in the second reaction stage at the final temperature mentioned must be long enough for the N-substituted intermediate products (aminobenzylaniline) to be quantitatively rearranged into polyamine containing only primary amino groups. This means that the reaction mixture is kept at the final temperature mentioned until no more aminobenzylaniline can be detected, for example by high-performance liquid chromatography.

At the beginning of the reaction, it is possible to premix aniline and hydrochloric acid and then to add the formaldehyde solution. It is also possible to initially react aniline and formaldehyde in the above-mentioned molar ratio in the absence of the acid (for example at 40° to 100° C.) to form the corresponding N,N'-disubstituted aminal, optionally to remove the water formed and the water introduced with the formaldehyde from the condensation product by phase separation, and then to add the hydrochloric acid to the product of this neutral preliminary reaction which is used in the first reaction stage of the process according to the invention.

The temperature of the reaction of formaldehyde with the aniline-hydrochloric acid mixture or of the product of the aniline-formaldehyde preliminary reaction with hydrochloric acid is an important process parameter so far as the quality of the end product is concerned. Since these reactions are highly exothermic, provision must be made for the effective dissipation of heat. In practice, the process according to the invention is preferably carried out under reduced pressure in directly cooled or, in accordance with German Patent No. 2,149,998, evaporation-cooled stirrer-equipped vessels. The appropriate choice of volume ensures an (average) residence time of at least 15 minutes and preferably of 30 to 90 minutes. Thereafter the remaining aniline is added and the mixture obtained is slowly heated as described above.

On completion of the second reaction stage, the reaction mixture is neutralized in known manner, for example with sodium hydroxide, the organic phase is separated from the salt solution, the excess aniline is distilled off from the organic phase and the polyamine mixture according to the invention recovered.

The process may be carried out either continuously or in batches. In the case of continuous operation, the second stage of the reaction may be advantageously carried out in a cascade of stirrer-equipped vessels followed by a pressure reactor or in suitably dimensioned tube or tower reactors providing the temperature profile described can be maintained.

The polyamines obtained may be further processed by phosgenation to form high-quality polyisocyanates of the diphenylmethane series which may be used as such, after admixture with other isocyanates or after suitable modification, as starting materials for rigid and flexible foams and for rigid and elastic moldings.

By virtue of their low content of polyisocyanates of relatively high functionality, the polyisocyanates obtained are also a valuable starting material for the production of pure 4,4'-diisocyanato-diphenylmethane and mixtures thereof with 2,4'-diisocyanato-diphenylmethane.

In the following Examples, all the percentages are percentages by weight.

EXAMPLES

EXAMPLE 1

(Comparison)

In a stirrer-equipped flask, 940 g (10.1 moles) of aniline are mixed with 146 g (1.2 moles) of 30% hydrochloric acid, followed by cooling to 35° C. 100 g (1 mole) of an aqueous 30% formaldehyde solution are then added with stirring, the temperature of the mixture being kept by cooling at 35° C. The mixture is kept at 35° C. for a total of 60 minutes, stirred at 45° C. for 60 minutes and then heated for another 60 minutes to 100° C. The resulting mixture is transferred to a pressure vessel, heated to 135° C. and kept at that temperature for 60 minutes. After cooling, the mixture is neutralized with 120 g (1.5 moles) of 50% sodium hydroxide. The salt solution formed is separated off by phase separation and water and free aniline are distilled off from the organic phase. The yield of polyamine mixture amounts to 191 g. The specific consumption of hydrochloric acid thus amounts by calculation to 229 g of 100% HCl per kg of polyamine.

The product has the following composition (MDA=abbreviation for diamino-diphenylmethane): 75.2% of 4,4'-MDA, 13.8% of 2,4'-MDA, 1.0% of 2,2'-MDA, 9.9% of polyamines.

EXAMPLE 2

(Comparison based on Example 1, Table I, Run 6 of U.S. Pat. No. 3,367,969)

In a stirrer-equipped flask, 279 g (3 moles) of aniline are mixed with 369 g (3.03 moles) of 30% hydrochloric acid. Thereafter, 100 g (1 mole) of a 30% aqueous formaldehyde solution are added with stirring at 40° C. The temperature is maintained for 30 minutes. 284.6 g (3.06 moles) of aniline are then added, the temperature is increased to 65° C. and the mixture is kept at that temperature for 3 hours. The reaction mixture is neutralized with 304 g (3.8 moles) of 50% sodium hydroxide. The salt solution formed is separated by phase separation and water and free aniline are distilled off from the organic phase. The yield of polyamine mixture amounts to 191 g. The specific consumption of hydrochloric acid amounts by calculation to 580 g of 100% HCl per kg of polyamine.

The product has the following composition: 85.2% of 4,4'-MDA, 5.0% of 2,4'-MDA, 0.1% of 2,2'-MDA, 9.8% of polyamine.

To produce the polyisocyanate, 100 g of the polyamine are first dissolved in 510 ml of chlorobenzene. A solution of 150 ml of liquid phosgene in 625 ml of chlorobenzene is prepared in a stirrer-equipped flask. The polyamine solution is added to the phosgene solution with stirring and the mixture obtained is heated to 130° C. over a period of 45 minutes during which hydrogen chloride and phosgene are removed in admixture as waste gas.

The solution thus obtained is freed from phosgene and chlorobenzene by distillation, the product having a final temperature of 240° C. The polyisocyanate mixture obtained is then characterized by the following data:
Chlorine content (%): 0.36
Absorbancy of a 5% solution in chlorobenzene at 430 nm: 0.348
Crystallization behavior at 25° C.: crystallizes in 8 hours

EXAMPLE 3

(According to the Invention)

In a stirrer-equipped flask, 260 g (2.8 moles) of aniline are mixed with 146 g (1.2 moles) of 30% hydrochloric acid, followed by cooling to 35° C. 100 g (1 mole) of a 30% aqueous formaldehyde solution are then added with stirring, the temperature of the mixture being kept by cooling at 35° C. The mixture is stirred at 35° C. for a total of 60 minutes. 680 g (7.3 moles) of aniline are then added, the mixture is heated to 45° C., stirred at 45° C. for 60 minutes and then heated for another 60 minutes to 100° C. The mixture is transferred to a pressure vessel, heated to 135° C. and kept at that temperature for 60 minutes. After cooling, the mixture is neutralized with 120 g (1.5 moles) of 50% sodium hydroxide. The salt solution formed is separated off by phase separation and water and free aniline are distilled off from the organic phase. The yield of polyamine mixture amounts to 191 g. The specific consumption of hydrochloric acid amounts by calculation to 229 g of 100% HCl per kg of polyamine.

The product has the following composition: 79.7% of 4,4'-MDA, 9.6% of 2,4'-MDA, 0.5% of 2,2'-MDA, 10.1% of polyamine.

The polyamine mixture is reacted with phosgene to form the isocyanate in exactly the same way as in Example 2. The polyisocyanate mixture obtained is characterized by the following data:
Chlorine content (%): 0.20
Absorbancy of a 5% solution in chlorobenzene at 430 nm: 0.232
Crystallization behavior at 25° C.: no crystallization after 8 days.

EXAMPLE 4

(According to the Invention)

In a stirrer-equipped flask, 260 g (2.8 moles) of aniline are reacted at 50° C. in the absence of acid with 100 g (1 mole) of formaldehyde in the form of a 30% aqueous solution. When the stirrer is switched off, the two-phase mixture separates into an upper aqueous phase and a lower organic phase.

The aqueous phase is separated off and the organic phase is mixed while stirring with 146 g (1.2 moles) of 30% hydrochloric acid, the temperature being kept at 35° C. The mixture is kept at 35° C. for 60 minutes, after which 857 g (9.2 moles) of aniline are added. The solution is then heated to 45° C. and, over a period of 60 minutes, to 100° C., subsequently transferred to a pressure vessel, heated therein to 140° C. and kept at that temperature for 20 minutes. After cooling, the mixture is neutralized with 120 g (1.5 moles) of 50% sodium hydroxide. The salt solution formed is separated off by phase separation and water and free aniline are distilled off from the organic phase. The yield of polyamine mixture amounts to 191 g. The specific consumption of hydrochloric acid amounts to 229 g of 100% HCl per kg of polyamine.

The product has the following composition: 79.5% of 4,4'-MDA, 10.8% of 2,4'-MDA, 0.35% of 2,2'-MDA and 9.35% of polyamine.

EXAMPLE 5

(Comparison)

The procedure is as in Example 1 using the following quantities: 15 moles (1395 g) of aniline, 1.2 moles (146 g) of 30% hydrochloric acid, 1 mole (100 g) of formaldehyde (30% aqueous solution) and 1.5 moles (120 g) of 50% sodium hydroxide. The polyamine mixture (191 g) has the following composition: 76.3% of 4,4'-MDA, 15.9% of 2,4'-MDA, 1.3% of 2,2'-MDA and 6.5% of polyamines.

EXAMPLE 6

(Continuous Procedure According to the Invention)

A continuous test arrangement consists of six 2-liter-capacity stirrer-equipped flasks arranged in the form of a cascade and a following 4-liter-capacity tube reactor operated under an excess pressure of 5 bars. The first stirrer-equipped flask is operated under reflux at a reduced pressure of 40 mbar so that it has a medium temperature of 34° C. The second stirrer-equipped flask is operated at 45° C., the third at 50° C., the fourth at 60° C., the fifth at 75° C. and the sixth at 95° C. From the sixth stirrer-equipped flask, the mixture is pumped into the tube reactor in which a medium temperature of 100° C. is adjusted at the beginning, steadily increasing and amounting at the outlet to 140° C. The acidic solution flowing off is cooled and collected.

1600 g/h of a mixture of 1025 g of aniline, 575 g of 30% hydrochloric acid and 394 g/h of a 30% aqueous formaldehyde solution are introduced into the first flask. This corresponds to a molar ratio of aniline to formaldehyde of 2.8:1 and to a degree of protonation of 43%. 4471 g/h of aniline are added to this mixture as it flows over into the second flask. This corresponds to a molar ratio of amine nitrogen atoms to chemically bound formaldehyde of 15:1. 6465 g of the mixture flowing off from the tube reactor are neutralized by the addition of 525 g of 50% sodium hydroxide. The salt solution formed is separated off by phase separation and water and free aniline are distilled off from the organic phase. The hourly yield of polyamine mixture amounts to 750 g. The specific consumption of acid amounts by calculation to 230 g of 100% HCl per kg of polyamine.

The product has the following composition: 4,4'-MDA 81.8%, 2,4'-MDA 9.3%, 2,2'-MDA 0.4%, polyamines 8.5%.

The polyamine mixture is reacted with phosgene to form the isocyanate in the same way as in Example 2. The polyisocyanate mixture obtained is characterized by the following data:

Chlorine content (%): 0.11

Absorbancy of a 5% solution in chlorobenzene at 430 nm: 0.158

Crystallization behavior at 25° C.: no crystallization after 8 days.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of polyisocyanates of the diphenylmethane series comprising:
   (a) at a temperature below 50° C., reacting either from 2.0 to 3.5 moles of aniline with 1 mole of formaldehyde in the presence of hydrochloric acid, or a condensation product in the presence of hydrochloric acid, said condensation product produced by reacting from 2.0 to 3.5 moles of aniline with 1 mole of formaldehyde in the absence of acid catalysts, the hydrochloric acid being present in an amount such that the degree of protonation is from 40 to 60%,
   (b) adding aniline to the product of step (a) in an amount such that the molar ratio of (i) amine nitrogen atoms in the form of free aniline and the reaction products formed in step (a) to (ii) formaldehyde bound in the form of methylene bridges in such reaction products rises to more than 10:1 and up to 20:1 with the degree of protonation decreasing correspondingly,
   (c) heating the reaction mixture of step (b) to allow the N-substituted intermediate products present to be completely rearranged into polyamines containing unsubstituted primary amino groups,
   (d) working up the reaction mixture of step (c) by neutralization of the acid and by distillation off of the excess aniline from the organic phase to thereby obtain polyamines having a high diamine content and a low 2,2'-diaminodiphenylmethane content, and
   (e) phosgenating the resultant polyamine.

2. A process as claimed in claim 1 characterized in that stage (a) is carried out at 30 to 40° C.

3. A process as claimed in claim 1, characterized in that the residence time of the reaction mixture in stage (a) is at least 15 minutes.

4. A process as claimed in claim 1, characterized in that the quantity of aniline added in stage (b) is such that the molar ratio of amine nitrogen atoms to bound formaldehyde amounts to between 11:1 and 16:1.

5. A process as claimed in claim 1, characterized in that, in stage (c), the reaction mixture is heated under pressure to temperatures of at least 130° C.

* * * * *